United States Patent

Murata et al.

[11] Patent Number: 5,578,600
[45] Date of Patent: Nov. 26, 1996

[54] STABLE LIQUID PREPARATION OF COMPLEX VITAMIN FOR INTERNAL USE

[75] Inventors: Yutaka Murata, Inba-mura; Yuko Kikuchi, Tokyo; Tomohiko Ohsugi; Noriko Aoki, both of Narita; Teiji Murata, Shisui-machi; Toshiaki Kurazumi, Narita; Akira Iwasa, Yotsukaido, all of Japan

[73] Assignee: SS Pharmaceutical Co., Ltd., Tokyo, Japan

[21] Appl. No.: 323,344

[22] Filed: Oct. 14, 1994

[30] Foreign Application Priority Data

Oct. 14, 1993 [JP] Japan .................................. 5-256767

[51] Int. Cl.$^6$ .................... A61K 31/51; A61K 31/415
[52] U.S. Cl. .................................... 514/276; 514/394
[58] Field of Search ........................ 514/276, 394

[56] References Cited

U.S. PATENT DOCUMENTS 4,806,354  2/1989  Green ................................. 424/687

OTHER PUBLICATIONS

Database WPI, Derwent Publications, AN–90–332333, JP–A–2 240 025, Sep. 25, 1990.

*Primary Examiner*—José G. Dees
*Assistant Examiner*—Mary C. Cebulak
*Attorney, Agent, or Firm*—Oblon, Spivak, McClelland, Maier & Neustadt, P.C.

[57] ABSTRACT

Described is a stable liquid preparation of complex vitamin for internal use. The preparation containing vitamin $B_1$ and vitamin $B_{12}$, and as a sweetening agent, a sugar alcohol. The pH of the preparation has been adjusted to 3.5 to 4.5.

8 Claims, No Drawings

1

STABLE LIQUID PREPARATION OF COMPLEX VITAMIN FOR INTERNAL USE

BACKGROUND OF THE INVENTION

1. Field of the Invention

This invention relates to a stable liquid preparation of complex vitamin for internal use, and more specifically to a liquid preparation of complex vitamin for internal use, which remains stable even when stored for a long period at room temperature.

2. Description of the Related Art

Like vitamin $B_6$, vitamin $B_1$ and vitamin $B_{12}$ are closely associated with nervous functions and are effective for the improvement of neuroses such as neuralgia, arthralgia, peripheral neuritis and peripheral paralysis. A variety of tablets and capsules added with these vitamins are therefore available on the market.

As a dosage form, a liquid preparation generally features that compared with such tablets and capsules, the liquid preparation is more readily absorbed in the body and is easier to take. Nonetheless, no stable liquid preparation containing both vitamin $B_1$ and vitamin $B_{12}$ has been available on the market. This is attributed to the poor storage stability of a liquid preparation containing both of them.

As causes for the poor storage stability of the liquid preparation added with both vitamin $B_1$ and vitamin $B_{12}$, it is known that the stable pH ranges of these vitamins in an aqueous solution are different, i.e., pH 2–4 for vitamin $B_1$ and pH 4.5–5 for vitamin $B_{12}$ and also that SR-containing decomposition products of vitamin $B_1$ extremely lower the stability of vitamin $B_{12}$.

Further, sucrose is generally used as a sweetening agent in liquid preparations for internal use. Sucrose may however lower the stability of vitamin $B_1$ and vitamin $B_{12}$, depending on its concentration and the pH. Liquid preparations for internal use are also added with a corrigent, a flavoring agent, a buffer agent, a preservative and the like. These additives may also give adverse effects on the stability, thereby making it more difficult to formulate a liquid preparation for internal use, which contains vitamin $B_1$ and vitamin $B_{12}$.

SUMMARY OF THE INVENTION

An object of the present invention is therefore to provide a liquid preparation for internal use, which contains vitamin $B_1$ and vitamin $B_{12}$ and remains stable even when stored for a long period at room temperature.

With the foregoing circumstances in view, the present inventors have proceeded with extensive research. As a result, it has been found that the above-described problem can be overcome by the addition of vitamin $B_1$ and vitamin $B_{12}$ to a particular solution base, leading to the completion of the present invention.

In one aspect of the present invention, there is thus provided a stable liquid preparation of complex vitamin for internal use, said preparation containing vitamin $B_1$ and vitamin $B_{12}$, comprising a sugar alcohol as a sweetening agent, the pH of said preparation having been adjusted to 3.5 to 4.5.

In the liquid preparation of complex vitamin for internal use according to the present invention, the activities of vitamin $B_1$ and vitamin $B_{12}$ are stably maintained without reduction even when the liquid preparation is stored for a long period at room temperature.

DETAILED DESCRIPTION OF THE INVENTION AND PREFERRED EMBODIMENTS

In the present invention, examples of vitamin $B_1$ include thiamine and thiamine derivatives such as fursultiamine, octotiamine, thiamine disulfide, bisbentiamine, bisbutitiamine, bisibutiamine and benfotiamine as well as their salts. Their hydrochlorides, nitrates and the like can be mentioned as these salts. Vitamin $B_1$ can preferably be added in an amount of 1–50 mg per 50 ml of the liquid preparation of complex vitamin for internal use (hereinafter called "the present preparation").

On the other hand, cyanocobalamin is preferred as vitamin $B_{12}$. It is preferred to add it in an amount of 1–5,000 µg in the present preparation.

Illustrative sugar alcohols usable as sweetening agents in the present invention include xylitol, maltitol and sorbitol. Since these sugar alcohols have the merit that they are hardly digestible and do not raise the blood sugar level, they are advantageous particularly for those suffering from diabetes mellitus or obesity. The sugar alcohol can be added preferably in an amount of 0.5–20 g, notably 1–15 g in the present preparation.

The above sugar alcohol has lower sweetness compared with sucrose, so that sucrose can be added to the liquid preparation of complex vitamin for internal use according to the present invention to supplement the sweetness. From the standpoint of stability of both the vitamins, it is necessary to limit the amount of added sucrose below 5 g in the present preparation.

As a pH regulator for adjusting the pH to 3.5–4.5 in the present invention, it is preferred to use an organic acid such as citric acid, malic acid, tartaric acid or succinic acid or a salt thereof which can reduce the bitterness of added ingredients and can make the preparation easier to take, although hydrochloric acid, sodium hydroxide or the like may be used. Regarding the amount of such an organic acid or a salt thereof in the liquid preparation of complex vitamin for internal use, it is preferred to limit its amount below 0.5 g in the present preparation.

In addition to the above-described essential ingredients, the liquid preparation of complex vitamin for internal use according to the present invention can also contain, as needed, optional ingredients such as, for example, drug efficacy ingredients such as $B_2$ vitamins, $B_6$ vitamins, E vitamins, nicotinic acid, nicotinamide, pantothenic acids, pantothenol, aminoethylsulfonic acid, anhydrous caffeine, γ-oryzanol, and crude drug ingredients, e.g., ginseng; solubilizers such as ethanol and polyoxyethylene-hydrogenated castor oil; preservatives such as benzoic acid and alkyl parabens (i.e., alkyl parahydroxybenzoates); coloring agents such as caramel; and perfumes.

The present invention will hereinafter be described in further detail by the following Examples, Comparative Examples and Test. It should however be borne in mind that the present invention is not limited to them in any way whatsoever.

EXAMPLE 1

The ingredients indicated in Table 1 were weighed in the amounts specified there and were then dissolved in purified water to give a total volume of 20 ml The resulting solution was filtered through a 0.45-µm membrane filter and filled in a 20-ml amber-colored glass bottle. The glass bottle was plugged and then subjected to sterilization at, 80° C. for 20 minutes, whereby a liquid preparation of complex vitamin for internal use was produced.

Incidentally, thiamine nitrate and cyanocobalamin were added 115% on their indicated amounts.

TABLE 1

| | | |
|---|---|---|
| Thiamine nitrate | | 10 mg |
| Cyanocobalamin | | 1,500 μg |
| Pyridoxine hydrochloride | | 100 mg |
| Nicotinamide | | 50 mg |
| Pantothenol | | 30 mg |
| D-Sorbitol solution (70%) | | 2,000 mg |
| Xylitol | | 2,500 mg |
| Malic acid | | 20 mg |
| Sodium hydroxide | Sufficient to adjust the pH to 4.0 | |
| Sodium benzoate | | 14 mg |
| Butyl parahydroxybenzoate | | 1 mg |
| Caramel | | 100 mg |
| Perfume | | trace |
| Purified water | Sufficient to produce | 20 ml |

EXAMPLE 2

Following the procedures of Example 1, a liquid preparation of complex vitamin for internal use was produced in accordance with the formulation shown in Table 2.

TABLE 2

| | | |
|---|---|---|
| Thiamine nitrate | | 10 mg |
| Cyanocobalamin | | 1,500 μg |
| Pyridoxine hydrochloride | | 50 mg |
| Nicotinamide | | 60 mg |
| Pantothenol | | 15 mg |
| D-Sorbitol solution (70%) | | 3,000 mg |
| Maltitol solution (75%) | | 4,000 mg |
| Citric acid | | 80 mg |
| Sodium citrate | Sufficient to adjust the pH to 4.0 | (15 mg) |
| Sodium benzoate | | 35 mg |
| Butyl parahydroxybenzoate | | 4 mg |
| Caramel | | 50 mg |
| Perfume | | trace |
| Purified water | Sufficient to produce | 50 ml |

EXAMPLE 3

Following the procedures of Example 1, a liquid preparation of complex vitamin for internal use was produced in accordance with the formulation shown in Table 3.

TABLE 3

| | | |
|---|---|---|
| Fursultiamine hydrochloride | | 6 mg |
| Cyanocobalamin | | 1,500 μg |
| Pyridoxine hydrochloride | | 10 mg |
| Riboflavin sodium phosphate | | 5 mg |
| Nicotinamide | | 25 mg |
| Anhydrous caffeine | | 50 mg |
| Aminoethylsulfonic acid | | 1,000 mg |
| D-Sorbitol solution (70%) | | 7,100 mg |
| Purified sucrose | | 4,000 mg |
| Citric acid | | 200 mg |
| Sodium citrate | Sufficient to adjust the pH to 3.7 | (120 mg) |
| Sodium benzoate | | 35 mg |
| Butyl parahydroxybenzoate | | 4 mg |
| Caramel | | 5 mg |
| Perfume | | trace |
| Purified water | Sufficient to produce | 50 ml |

EXAMPLE 4

Following the procedures of Example 1, a liquid preparation of complex vitamin for internal use was produced in accordance with the formulation shown in Table 4.

TABLE 4

| | | |
|---|---|---|
| Fursultiamine hydrochloride | | 6 mg |
| Cyanocobalamin | | 1,500 μg |
| Pyridoxine hydrochloride | | 10 mg |
| Nicotinamide | | 50 mg |
| Anhydrous caffeine | | 50 mg |
| Liquid ginseng extract | | 0.6 ml |
| Liquid polygonati rhizoma extract | | 0.4 ml |
| Liquid cistanchis herba extract | | 0.3 ml |
| D-Sorbitol solution (70%) | | 5,000 mg |
| Xylitol | | 1,500 mg |
| Purified sucrose | | 2,000 mg |
| Citric acid | Sufficient to adjust the pH to 4.2 | (100 mg) |
| Sodium citrate | | 120 mg |
| Polyoxyethylene-hydrogenated castor oil 60 | | 10 mg |
| Sodium benzoate | | 35 mg |
| Butyl parahydroxybenzoate | | 4 mg |
| Caramel | | 5 mg |
| Perfume | | trace |
| Purified water | Sufficient to produce | 50 ml |

COMPARATIVE EXAMPLE 1

Following the procedures of Example 1, a liquid preparation of complex vitamin for internal use was produced in accordance with the formulation shown in Table 5.

TABLE 5

| | | |
|---|---|---|
| Thiamine nitrate | | 10 mg |
| Cyanocobalamin | | 1,500 μg |
| Pyridoxine hydrochloride | | 50 mg |
| Nicotinamide | | 60 mg |
| Pantothenol | | 15 mg |
| Purified sucrose | | 2,000 mg |
| Isomerized sugar | | 6,500 mg |
| Citric acid | | 80 mg |
| Sodium citrate | Sufficient to adjust the pH to 4.0 | |
| Sodium benzoate | | 35 mg |
| Butyl parahydroxybenzoate | | 4 mg |
| Caramel | | 50 mg |
| Perfume | | trace |
| Purified water | Sufficient to produce | 50 ml |

COMPARATIVE EXAMPLE 2

Following the procedures of Example 1, a liquid preparation of complex vitamin for internal use was produced in accordance with the formulation shown in Table 6.

TABLE 6

| | | |
|---|---|---|
| Thiamine nitrate | | 10 mg |
| Cyanocobalamin | | 1,500 μg |
| Pyridoxine hydrochloride | | 50 mg |
| Nicotinamide | | 60 mg |
| Pantothenol | | 15 mg |
| Purified sucrose | | 7,500 mg |
| Citric acid | | 250 mg |
| Sodium citrate | Sufficient to adjust the pH to 5.0 | |
| Sodium benzoate | | 35 mg |
| Butyl parahydroxybenzoate | | 4 mg |
| Caramel | | 50 mg |

TABLE 6-continued

| Perfume | | trace |
|---|---|---|
| Purified water | Sufficient to produce | 50 ml |

TEST

The liquid preparations of complex vitamin for internal use, which had been produced in Examples 1–4 and Comparative Examples 1–2, respectively, were stored at room temperature for 12 months and 24 months, followed by quantitative analyses of vitamin $B_1$ and vitamin $B_{12}$. The results of the stability test of vitamin $B_1$ are shown in Table 7, whereas the results of the stability test of vitamin $B_{12}$ are presented in Table 8.

The quantitative analyses were conducted by high performance liquid chromatography, and the stability of each liquid preparation is indicated by a value (%) on the indicated amount.

MEASUREMENT OF STABILITY OF VITAMIN $B_1$

TABLE 7

| | After stored for 12 months | After stored for 24 months |
|---|---|---|
| Example 1 | 107.7 | 100.7 |
| Example 2 | 108.8 | 100.8 |
| Example 3 | 110.9 | 104.1 |
| Example 4 | 109.6 | 102.7 |
| Comp. Ex. 1 | 104.5 | 95.2 |
| Comp. Ex. 2 | 96.3 | 78.9 |

At the time of production: 115.0%

MEASUREMENT OF STABILITY OF VITAMIN $B_{12}$

TABLE 8

| | After stored for 12 months | After stored for 24 months |
|---|---|---|
| Example 1 | 104.2 | 93.7 |
| Example 2 | 105.8 | 96.0 |
| Example 3 | 107.0 | 99.0 |
| Example 4 | 109.6 | 102.0 |
| Comp. Ex. 1 | 99.5 | 83.0 |
| Comp. Ex. 2 | 101.0 | 88.7 |

At the time of production: 115.0%

RESULTS

As is evident from Table 7 and Table 8, vitamin $B_1$ and vitamin $B_{12}$ in each liquid preparation of complex vitamin for internal use according to this invention retained high Stability.

We claim:

1. A stable liquid preparation of a complex vitamin for internal use, said liquid preparation having an adjusted pH of 3.5 to 4.5, consisting essentially of:

a) a vitamin combination of at least vitamins $B_1$ and $B_{12}$;

b) a sugar alcohol as a sweetening agent; and c) at least one other component selected from the group consisting of drug efficacy ingredients, crude drug ingredients, solubilizers, preservatives, coloring agents and perfumes.

2. The preparation according to claim 1, wherein vitamin $B_1$ is thiamine or a derivative thereof or a salt of thiamine or the thiamine derivative; and vitamin $B_{12}$ is cyanocobalamine.

3. The preparation according to claim 1 or 2, wherein said sugar alcohol is xylitol, maltitol or sorbitol.

4. The preparation according to claim 1, wherein citric, malic, tartaric or succinic acid or a salt thereof regulates the pH of the preparation to within the stated range in an amount not greater than 0.5 g per preparation.

5. The preparation according to claim 1, wherein the amount of said sugar alcohol in the preparation ranges from 0.5–20 g per 50 ml of liquid preparation.

6. The preparation according to claim 1, wherein said amount of sugar alcohol ranges from 1–15 g.

7. The preparation according to claim 1, wherein the amount of said vitamin $B_{12}$ ranges from 1–5,000 μg per 50 ml of liquid preparation.

8. The preparation according to claim 1, wherein the amount of said vitamin $B_1$ ranges from 1–50 mg per 50 ml of liquid preparation.

* * * * *